United States Patent [19]
Pinchuk

[11] Patent Number: 5,415,664
[45] Date of Patent: May 16, 1995

[54] METHOD AND APPARATUS FOR INTRODUCING A STENT OR A STENT-GRAFT

[75] Inventor: Leonard Pinchuk, Miami, Fla.

[73] Assignee: Corvita Corporation, Miami, Fla.

[21] Appl. No.: 220,187

[22] Filed: Mar. 30, 1994

[51] Int. Cl.$^6$ ............................................. A61M 29/00
[52] U.S. Cl. ................................. 606/108; 606/198; 604/280
[58] Field of Search .................. 604/104, 107–109, 604/280, 281; 606/108, 191, 198, 200

[56] References Cited

U.S. PATENT DOCUMENTS

| | | | |
|---|---|---|---|
| 4,787,899 | 11/1988 | Lazarus | 623/1 |
| 5,026,377 | 6/1991 | Burton et al. | 606/108 |
| 5,078,720 | 1/1992 | Burton et al. | 606/108 |
| 5,160,341 | 11/1992 | Brenneman et al. | 606/198 |
| 5,201,757 | 4/1993 | Heyn et al. | 606/108 |
| 5,235,966 | 8/1993 | Jamner | 128/20 |
| 5,242,399 | 9/1993 | Lau et al. | 604/104 |
| 5,279,561 | 1/1994 | Roucher et al. | 604/96 |
| 5,290,295 | 3/1994 | Querals et al. | 606/108 |
| 5,312,415 | 5/1994 | Palermo | 606/108 |

Primary Examiner—Corrine Maglione
Attorney, Agent, or Firm—David P. Gordon

[57] ABSTRACT

A stent, stent-graft or endolumimal graft introducer includes a hollow tube having a proximal end and a distal end and a cup-like end cap for covering the distal end. The cap is coupled to a control member which extends through the hollow tube. The proximal ends of the tube and the control member are coupled to an actuation device for effecting relative movement of the the tube and control member to move the cap relative to the distal end of the tube. The distal end of a stent or stent-graft is inserted into the cup-like cap and the actuation device is manipulated to move the cap and the distal end of the tube together, thereby gripping the distal end of the stent. The introducer is inserted into a sheath and pulls the distal end of the stent into the sheath, thereby stretching it to its reduced diameter. The sheath containing the stent and the introducer is maneuvered to the site for deployment of the stent. The introducer is held in a stationary position and the sheath is withdrawn so that the a portion of the stent is released from the sheath. The introducer, stent, and sheath can then be moved as one so that the stent is precisely located before it is deployed. When the stent is in the precise location, the sheath is completely withdrawn from the stent. The actuation device is then manipulated to release the distal end of the stent from the introducer. The introducer is removed through the lumen of the stent.

25 Claims, 6 Drawing Sheets

METHOD AND APPARATUS FOR INTRODUCING A STENT OR A STENT-GRAFT

BACKGROUND OF THE INVENTION

1. Field of the Invention

This invention relates broadly to the delivery and deployment of a transluminal prosthesis. More particularly, this invention relates to a method and apparatus for delivering and deploying a flexible tubular prosthesis having a diameter which is variable by axial movement of the ends of the prosthesis.

2. State of the Art

Figure 1:
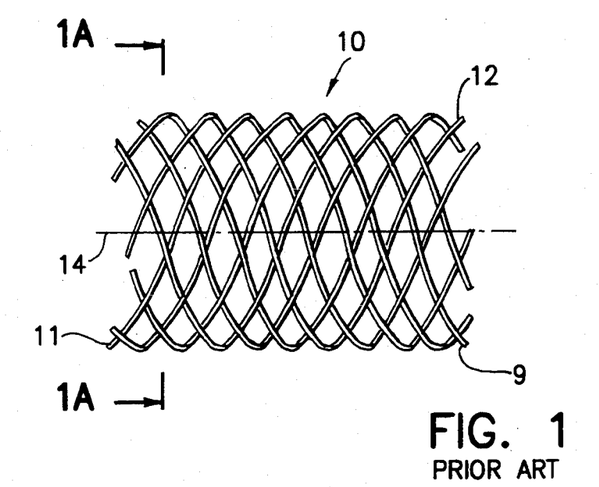
FIG. 1 is a broken side elevation view of a prior art stent expanded in a non-stressed position.
Figure 1A:
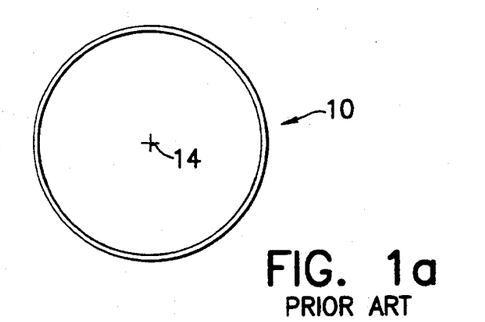
FIG. 1a is a cross sectional view along line 1A—1A of FIG. 1.
Figure 2:
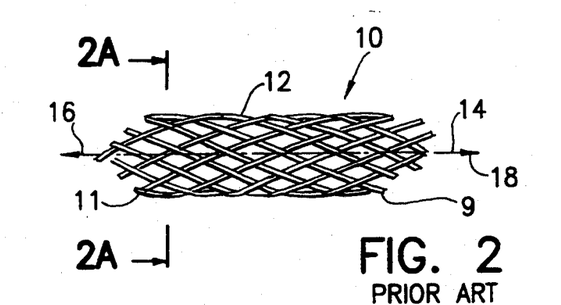
FIG. 2 is a broken side elevation view of a prior art stent stretched and contracted.
Figure 2A:
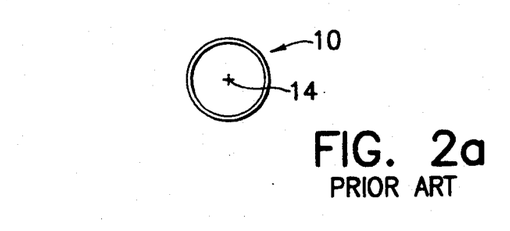
FIG. 2a is a cross sectional view along line 2A—2A of FIG. 2.

Transluminal prostheses are well known in the medical arts for implantation in blood vessels, biliary ducts, or other similar organs of the living body. These prostheses are commonly known as stents and are used to maintain, open, or dilate tubular strictures or to support tubular structures that are being anastomosed. When bio-compatible materials are used as a covering or lining for the stent, the prosthesis is called a stent-graft or endoluminal graft. A typical state of the art stent such as disclosed in U.S. Pat. No. 4,655,771 to Wallsten or in U.K. Patent Number 1,205,743 to Didcott is shown herein in prior art FIGS. 1, 1a, 2, and 2a. Didcott and Wallsten disclose a tubular body stent 10 composed of wire elements 12, each of which extends in a helical configuration with the centerline 14 of the stent 10 as a common axis. Half of the elements 12 are wound in one direction while the other half are wound in an opposite direction. With this configuration, the diameter of the stent is changeable by axial movement of the ends 9, 11 of the stent. Typically, the crossing elements form a braid-like configuration and are arranged so that the diameter of the stent 10 is normally expanded as shown in FIGS. 1 and 1a. The diameter may be contracted by pulling the ends 9, 11 of the stent 10 away from each other as shown by the arrows 16, 18 in FIG. 2. When the ends of the body are released, the diameter of the stent 10 self-expands and draws the ends 9, 11 of the stent closer to each other.

Figures 3, 4:
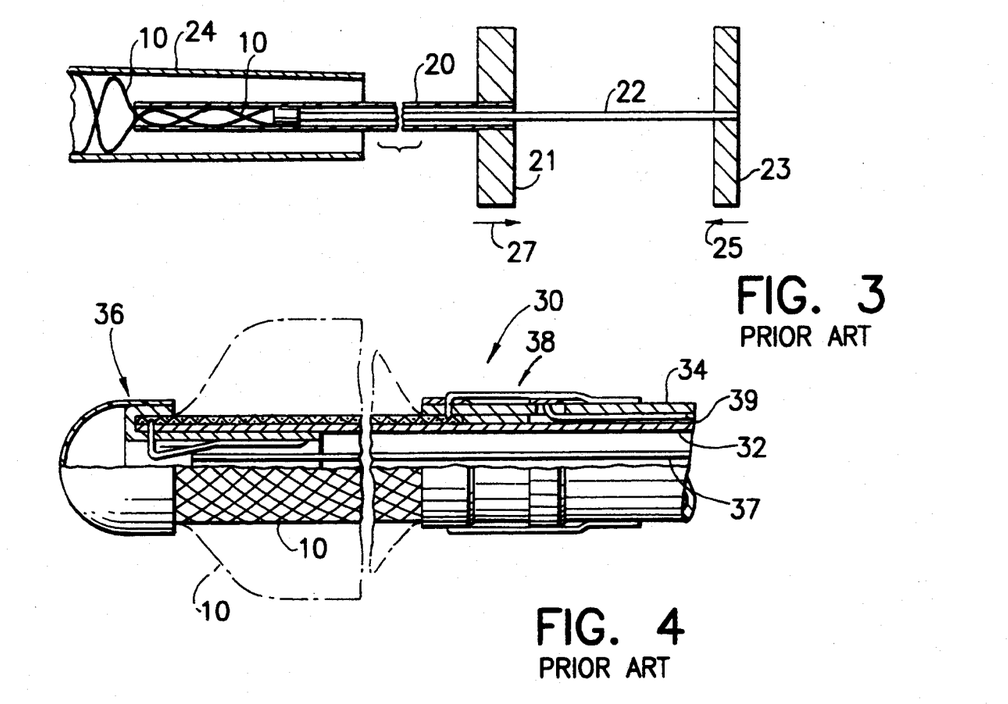
FIG. 3 is a broken cross sectional view of a first prior art stent delivery and deployment apparatus.
FIG. 4 is a broken cross sectional view of the distal end of a second prior art stent delivery and deployment apparatus.

A stent such as the ones described by Didcott and Wallsten may be introduced into the body by stretching it until its diameter is reduced sufficiently so that it can be fed into a catheter. The stent is delivered through the catheter to the site of deployment and then released from the catheter whereupon it self-expands. A simple delivery device for locating and deploying the stent is shown in prior art FIG. 3 and includes a flexible catheter 20 having a proximal handle 21 and a flexible plunger 22 having a proximal handle 23. As shown in FIG. 3, the stent 10 is partially inserted into the distal end of the catheter 20 and partially expanded around the inner wall of an artery 24. Those skilled in the art will appreciate that prior to delivery and deployment, the stent is completely inserted into the distal end of the catheter 20 and the distal end of the catheter is positioned at the site of deployment, such as artery 24. The handles 21, 23 of the catheter 20 and the plunger 22 are moved relative to each other as shown by the arrows 25, 27 thereby moving the catheter and plunger relative to each other and pushing the stent 10 out of the distal end of the catheter. It will be appreciated, however, that this prior art delivery device is deficient in several respects. First, pushing the stent 10 with the plunger 22 can damage the wires comprising the stent. In particular, the wires can kink or bunch up preventing proper deployment of the stent. The ends of the wires can bend inward occluding the lumen of the stent. Furthermore, the wires can break and cause the stent to partially come apart. Second, by releasing the distal end of the stent first, the stent can no longer be positioned in the distal direction. In particular, the ends of the wires of the distal end of the stent will typically lodge themselves in the wall of the artery 24 and prohibit movement of the stent in the distal direction. Third, as the stent is released from the catheter, it contracts in length as it expands diametrically. Therefore, care must be taken to position the distal end of the catheter further into the artery than the stent is to be deployed so that when the stent is released, its length will contract to the location where it is to be deployed. This substantially complicates proper location of the stent. Fourth, this prior art delivery device is difficult to load. The stent must be manually stretched and carefully fed into the catheter without bending the ends of its wires or allowing the ends of the wires to penetrate the wall of the catheter. Fifth, when a coated stent is deployed from its distal end first, retrograde to blood flow, for example if it is maneuvered from the femoral artery to the aorta, the distal end of the stent opens first, thereby being subjected to the full force of flowing blood. This blood flow can cause the stent to compress prior to lodging in the vessel wall, thus further complicating the accuracy of the deployment.

Another known device for delivering and deploying a stent is shown in prior art FIG. 4. The prior art stretching device 30 of FIG. 4 has an inner flexible tube 32 and an outer flexible tube 34 which are coupled at their proximal ends to an actuation means (not shown) for producing relative axial movement of the tubes. The inner tube 32 is provided with a pointed gripping device 36 at its distal end, and the outer tube 34 is provided with a similar gripping device 38 at its distal end. Both gripping devices 36, 38 are operated by respective control wires 37, 39 which extend to the proximal actuation means (not shown). The broken view of prior art FIG. 4 shows the stent 10 in a dotted line prior to axial stretching. Those skilled in the art will appreciate that the ends of the stent 10 are attached by the gripping means 36, 38 to the distal ends of the inner and outer tubes 32, 34 and the tubes are axially moved to stretch the stent 10 to the size shown in solid lines in FIG. 4. The tubes carrying the stretched stent are delivered to the site of deployment and moved relative to each other to expand the stent. The gripping means 36, 38 are then released and the stent expands diametrically while contracting axially. This device allows for reasonably precise location of the stent since the stent can be partially expanded diametrically at its center by movement of the tubes before releasing the gripping means. However, the prior art delivery device of FIG. 4 has a very complex and expensive construction. It is also difficult to manipulate and the pointed gripping means can damage the ends of the stent. In addition, with the delivery device of FIG. 4, the stent-graft which is being delivered is exposed to blood during its insertion, and this can result in a thromboembolism. Furthermore, the numerous wires required to maintain the stent-graft in its compressed state increases the profile of the stent-graft. In order to maintain the stent-graft in its compressed state, the inner members must be under extreme compression, thereby rendering the device stiff and difficult to maneuver.

SUMMARY OF THE INVENTION

It is therefore an object of the invention to provide a method for introducing a stent and a stent delivery system Which will not damage the stent.

It is also an object of the invention to provide a stent introducing apparatus which is easy to use.

It is another object of the invention to provide a stent introducing apparatus which is simple to manufacture.

It is still another object of the invention to provide a method and apparatus for introducing a stent which allows for precise location of the stent.

It is yet another object of the invention to provide a stent introducer which is easily bendable and can track a guide wire.

It is also an object of the invention to provide a stent introducer which will open from its downstream end first.

It is still another object of the invention to provide a stent introducer which has a soft tip.

In accord with these objects which will be discussed in detail below, the stent delivery and deployment apparatus of the present invention includes an introducer which is removably insertable through a hollow body such as a blood vessel, a sinus tract, an esophagus, a trachea, a bile duct, an anus, an intestine, or the like. The introducer includes three concentric tubes: a hollow tube having a proximal end and a distal end; an inner tubular actuation member having a proximal end and a distal end; and an outer sheath. A cup-like gripping member is rigidly attached to the distal end of the tubular actuation member. The proximal ends of the hollow tube and the actuation member are coupled to an actuation device which effects relative movement of the hollow tube and the actuation member. In this manner, the cup-like gripping member moves relative to the distal end of the hollow tube, thereby forming a clamping or gripping mechanism between the cup-like member and the distal end of the hollow tube.

According to the method of the invention, the distal end of a stent or stent-graft is inserted into the cup-like member and the actuation device is manipulated to move the cup-like member and the distal end of the hollow tube together, thereby gripping the distal end of the stent. The distal end of the introducer is inserted into the sheath and pulls the distal end of the stent into the sheath, thereby stretching and radially compressing it to its reduced diameter. The sheath containing the stent and the remainder of the introducer is maneuvered to the site for deployment of the stent. The introducer is held in a stationary position and the sheath is pulled partially back towards the proximal end of the introducer so that a middle portion of the stent is released from the sheath. The introducer, stent, and sheath can then be moved as one so that the stent is precisely located before it is deployed. When the stent is in a precise desired location, the introducer is held in a stationary position and the sheath is pulled back further to release the proximal end of the stent. The actuation device is then manipulated to release the distal end of the stent from the cup-like cap member and the distal end of the hollow tube. After this, the introducer is free to be removed through the lumen of the diametrically expanded stent.

Preferred aspects of the apparatus of the invention include: providing a latching or ratchet means on the actuation device so that the introducer can be locked in the stent gripping position until the stent is at the deployment site; providing the distal end of the hollow tube of the introducer with a frustroconical tip; and providing a cup-like cap with a mating frustroconical interior which matingly receives the frustroconical tip of the hollow tube of the introducer.

According to another embodiment of the invention, the cup-like cap and the control member are provided with an inner bore through which a guide wire may be inserted and used to guide the apparatus to the site of stent deployment. Other optional features of the apparatus include: controlling the sheath with one or more wires; making the distal end of the cup-like cap soft to reduce patient trauma; including radiopaque markers on the introducer so that it can be seen under fluoroscopy; and providing slippery surfaces on the sheath and the introducer to facilitate release of the stent. The apparatus may be disposable or reusable and may be dimensioned to suit particular applications.

Additional objects and advantages of the invention will become apparent to those skilled in the art upon reference to the detailed description taken in conjunction with the provided figures.

DETAILED DESCRIPTION OF THE PREFERRED EMBODIMENTS

Figures 5, 5A:
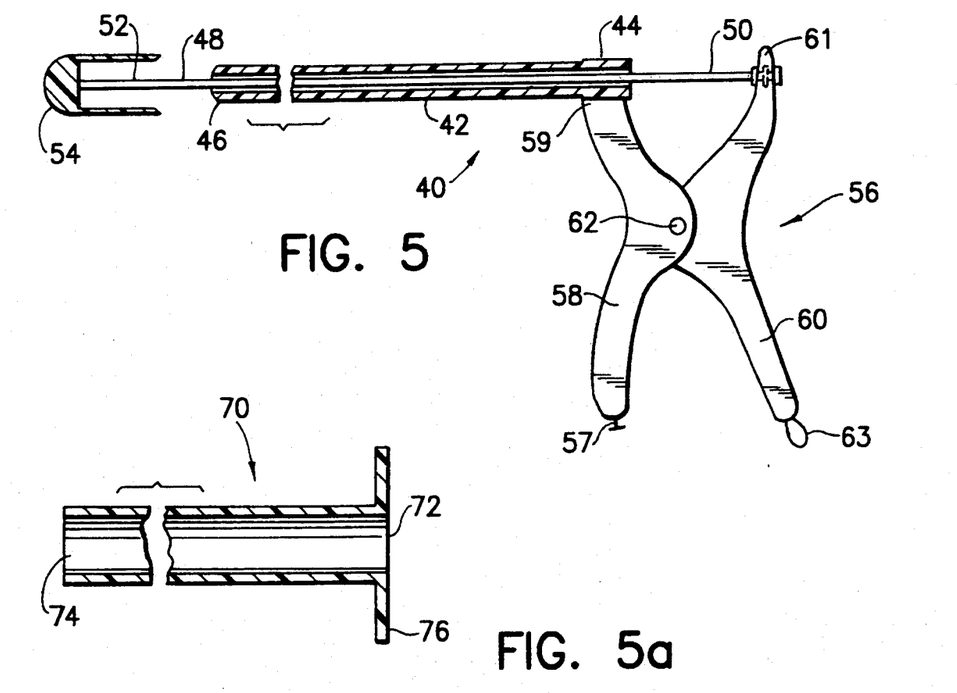
FIG. 5 is a broken side elevation view in partial section of a first embodiment of a stent introducer according to the invention.
FIG. 5a is a broken cross sectional view of a sheath for use with the stent introducer according to the invention.

Referring now to FIGS. 5 and 5a, a first embodiment of the stent delivery apparatus of the invention includes a stent introducer 40 and a sheath 70. The stent introducer 40 according to the invention includes a hollow tube 42 having a proximal end 44 and a distal end 46. A control member 48, which may take the form of a rod, has a proximal end 50 and a distal end 52. The control member 48 extends through the hollow tube 42 and is coupled at its distal end 52 to the interior of a cup-like cap 54. A lever actuator 56 has a first handle member of finger grip means 58 and a second handle or lever member or finger grip means 60 which are pivotally coupled to each other by a pivot pin 62. An upper end 59of the first handle member 58 is coupled to the proximal end 44 of the hollow tube 42. An upper end 61 the lever member 60 is coupled to the proximal end 50 of the control member 48. From the foregoing, those skilled in the art will appreciate that when the handle member 58 and lever 60 are squeezed together, the control member 48 is moved proximally through the hollow tube 42 and the end cap 54 is brought into a position where it covers and engages the distal end 46 of the hollow tube 42. Depending on the particular application, the hollow tube and the control member may be made rigid or flexible. Suitable materials for the tube and the control member include polyethylene, polyurethane, NYLON, TEFLON, metal springs, coils or braids, metal tubing, reinforced plastics, or combinations of these. If the introducer is to be made rigid, the tube and control member may be made of stainless steel, nitinol or the like.

As will be described in detail below with reference to FIGS. 9 and 9a, according to the method of the invention, the distal end of a stent is captured and held between the end cap 54 and the distal end 46 of the hollow tube 42 when the handle and lever members are squeezed together as described above. In order to hold the end cap against the distal end of the tube, the handle and,lever members are preferably provided with locking means such as a hook 57 and eyelet 63. With the distal end of a stent captured and held between the end cap 54 and the distal end 46 of the hollow tube 42, the introducer 40 is inserted into the proximal end 72 of a sheath 70 (FIG. 5a) until the end cap 54 extends just beyond the distal end 74 of the sheath. The sheath, which is preferably made of 75D polyurethane, NYLON, PET, PFE, PTFE, polyethylene, or the like, is provided with a proximal gripping flange 76 to aid in this operation as described in further detail below with reference to FIGS. 10 and 10a. Moreover, the proximal end 72 of the sheath 70 may be provided with a valve means (not shown) to prevent blood from leaking out of the sheath.

Figure 6:
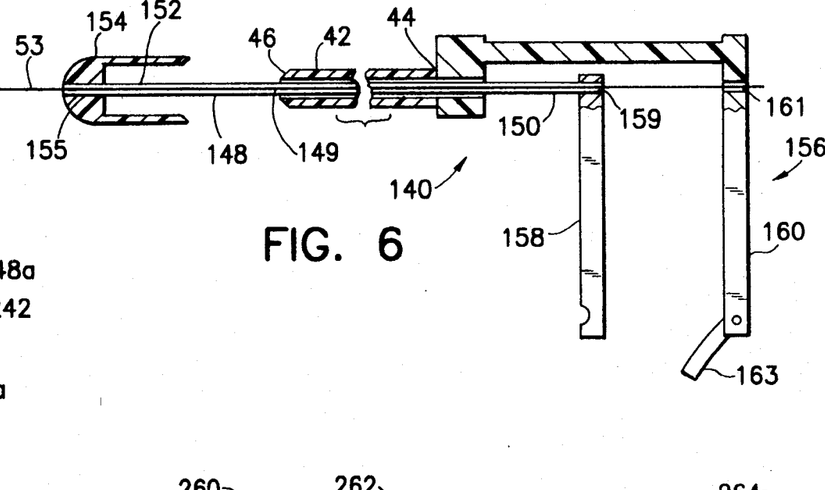
FIG. 6 is a broken cross sectional view of a second embodiment of a stent introducer according to the invention.

Turning now to FIG. 6, a second embodiment of the stent introducer 140 has a similar hollow tube 42 with a proximal end 44 and a distal end 46. In this embodiment, the end cap 154 is provided with a central bore 155, and the control member 148 is similarly provided with a central bore 149 which extends from its proximal end 150 to its distal end 152. The actuator handle or finger grip means 156 includes an inverted L-shaped member 160 which is coupled to the proximal end 44 of the hollow tube 42, and a sliding member or finger grip means 158 which is coupled to the proximal end 150 of the control member 148. Those skilled in the art will appreciate that when the actuator members 158, 160 are squeezed together, the end cap 154 covers and engages the distal end 46 of the tube 42. A latch 163 is provided on the lower portion of the inverted L-shaped member 160 for holding the actuator handle members together as described above with reference to the first embodiment. Both members 158 and 160 are provided with bores 159, 161, respectively, through which a guide wire 53 may be inserted. Guide wire 53 extends through the central bore 149 of the control member 148 and the central bore 155 of the end cap 154 to the deployment site (not shown) and helps to guide the introducer 140 to the deployment site.

Figure 7:
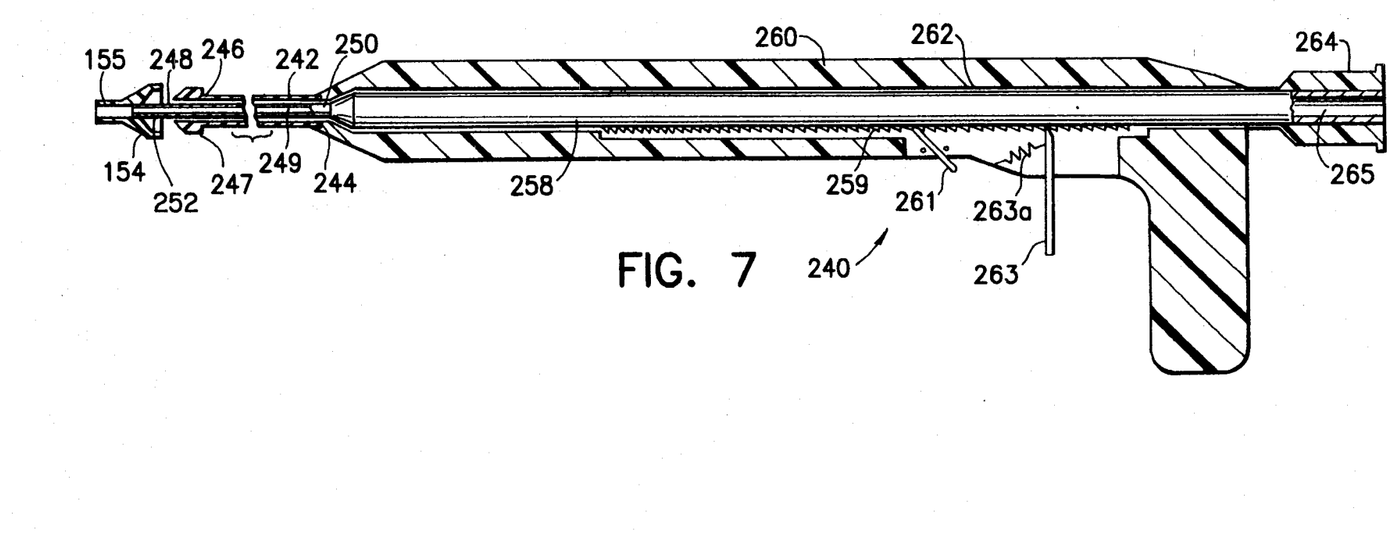
FIG. 7 is a broken cross sectional view of a third embodiment of a stent introducer according to the invention.

FIG. 7 shows another embodiment of an introducer 240 according to the invention. The introducer 240 includes a flexible coil 242 which is coupled at its proximal end 244 to a pistol grip 260. The distal end 246 of coil, 242 is provided with a tapered capturing or locking member or cover 247 having a substantially frustroconical distal end. A flexible control member 248 extends through the coil 242. The control member 248 has a cylinder 258 coupled to its proximal end 250 and an end cap 154 coupled to its distal end 252. The cylinder 258 is provided with a serrated surface or rack 259 along a proximal portion thereof and is mounted in a throughbore 262 in the pistol grip or finger grip means 260. A proximal handle portion 264 is mounted on the proximal end of the cylinder 258 and is accessible outside the pistol grip as seen in FIG. 7. The pistol grip 260 is provided with a reversible pawl 261 and a ratchet trigger or finger grip means 263 which is biased by a return spring 263a. Those skilled in the art will appreciate that when the reversible pawl 261 is set in a first position, the cylinder 258 may be advanced in the proximal direction relative to the pistol grip 260 by pulling on the handle portion 264 so that the end cap 154 is brought into engagement with and covers the tapered locking member 247. The pawl 261 may also be set in a second position such that movement of the trigger 263 causes the end cap 154 to move away from the tapered locking member 247. The control member 248 is provided with a longitudinal throughbore 249 which communicates with a central throughbore 155 in the end cap 154 and a throughbore 265 in the cylinder 258. A guide wire (not shown) may be inserted through the central bore 155, the longitudinal bore 249 and the throughbore 265 in order to aid in guiding the introducer 240 to the site of deployment.

Figure 7A:
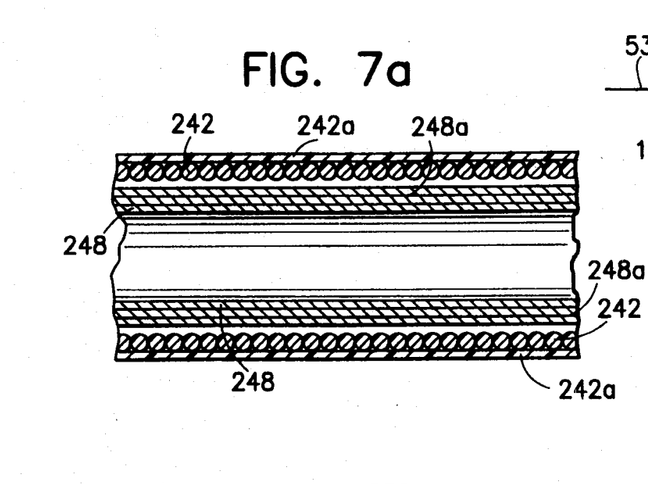
FIG. 7a is an enlarged broken cross sectional view of a portion of FIG. 7.

FIG. 7a shows an enlarged cross section of a portion of the coil 242 and the control member 248. The control member 248 is preferably a catheter-like structure with a reinforced braid 248a to limit axial stretching. The coil 242 may also have a thin flexible coating 242a on its outer surface to prevent blood leakage through the coil.

Figure 8:
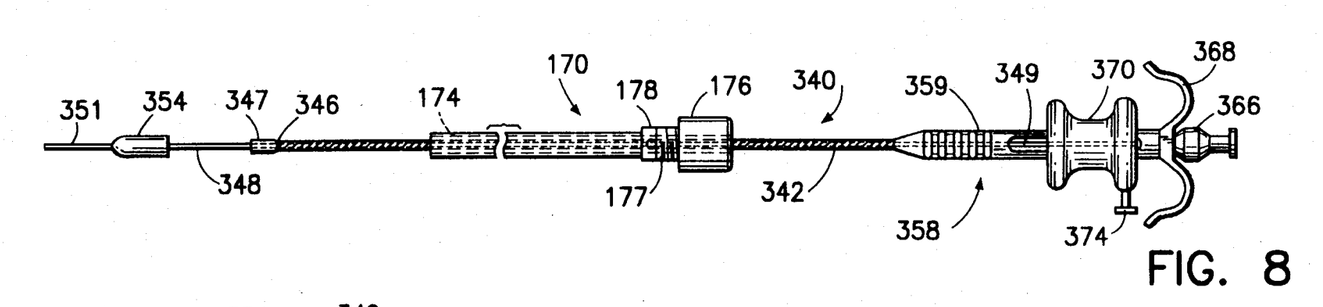
FIG. 8 is a broken cross sectional view of the distal end of a fourth embodiment of a stent introducer according to the invention together with a sheath.
Figure 8A:
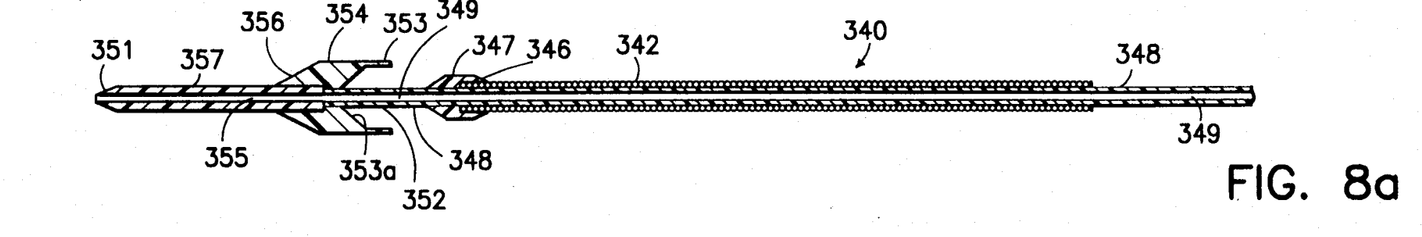
FIG. 8a is an enlarged broken cross sectional view of the distal portion of the stent introducer of FIG. 8.
Figure 8B:
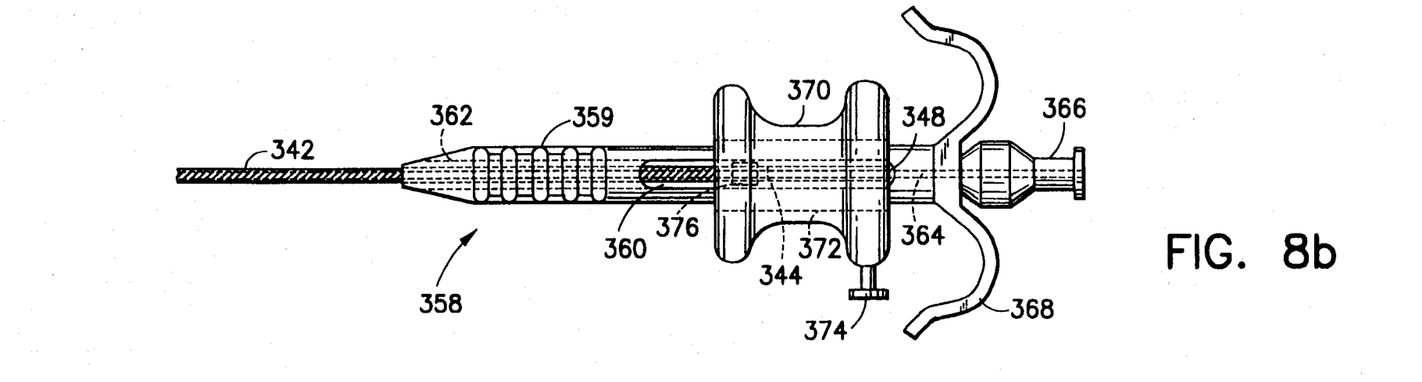
FIG. 8b is an enlarged broken side elevation view of the proximal portion of the stent introducer of FIG. 8.

FIGS. 8, 8a and 8b show a presently preferred embodiment of the stent introducer 340 according to the invention. The introducer 340 includes a flexible coil 342 and a coaxial control member 348 which extends through the coil 342. The proximal ends of the coil and control member are coupled to a slotted handle 358 such as the type used in endoscopic biopsy forceps. The distal end 346 of coil 342 is provided with a tapered capturing or locking member 347 having a substantially frustroconical distal end.

As shown in FIG. 8, a preferred sheath 170 is provided with a central throughbore 174 and a proximal collar 178 carrying a sheath fastener hub 176. The hub 176 is provided with internal threads and an O-ring washer (not shown). The proximal collar 178 is provided with external threads 177 which engage the internal threads of the hub 176. The hub is tightened against the collar by rotational engagement of their respective threads. When the hub is thus tightened the O-ring forms a hemostasis valve between the sheath and the introducer to prevent blood leakage out the proximal end of the sheath.

FIG. 8a shows the distal portion of a presently preferred embodiment of the stent introducer according to the invention. This embodiment is similar to the embodiment described above with a flexible coil 342 having a frustroconical tapered capturing or locking member 347 at its distal end 346. The control member 348 is preferably made from stiff-plastic such as polyurethane having a Shore 75D hardness or a steel braid reinforced polyurethane tube. The distal end 352 of the control member 348 is provided with a rigid cap 354 which has a proximal cylindrical portion 353, an interior frustroconical portion 353a, an Outer frustroconical portion 356, and a distally extending soft catheter tip 357. The soft catheter tip 357 is preferably provided with a tapered distal end 351 and an internal throughbore 355 which communicates with a longitudinal bore 349 in the control member 348. Bores 355 and 349 are provided for insertion of a guide wire as well as for the injection of radiopaque dyes as described in more detail below. It will be appreciated that this embodiment of the distal portion of the stent introducer can be used with any one of the actuation handles described above with reference to FIGS. 5–8.

As shown in FIG. 8b, the slotted handle 358 is provided with a shaft 359 having a central slot 360 which communicates with a distal throughbore 362 and a proximal throughbore 364. The proximal throughbore 364 preferably terminates in a proximal luer coupling 366 and a hand grip or finger grip means 368 is provided on a proximal portion of the shaft 359 between the slot 360 and the luer coupling 366. A displaceable spool or finger grip means 370 having a central throughbore 372 is slideably disposed on the shaft 359. The spool 370 is also preferably provided with a locking set screw 374 for locking its position on the shaft 359.

The proximal end of the control member 348 is coupled to the handle 358 preferably by bonding it to the proximal throughbore 364 so that the bore 349 in the control member 348 is in communication with the luer coupling 366. The proximal end 344 of the coil 342 is coupled to the spool 370 by means of a cross block 376. The coil passes freely through the distal bore 362 in the shaft 359. From the foregoing, it will be understood that movement of the spool 370 relative to the shaft 359 effects a movement of the coil 342 relative to the control member 348, and thereby effects movement of the locking member 347 relative to the cap 354. A guide wire (not shown) may be inserted through the central bore 355, the longitudinal bore 349 and the luer coupling 366 in order to aid in guiding the introducer 340 to the site of deployment. A source of radiopaque fluid may be coupled to the luer 366 for injection at the deployment site. A hemostasis value may also be connected to luer 366 to prevent blood from leaking between the guidewire and the control member.

Figure 9:
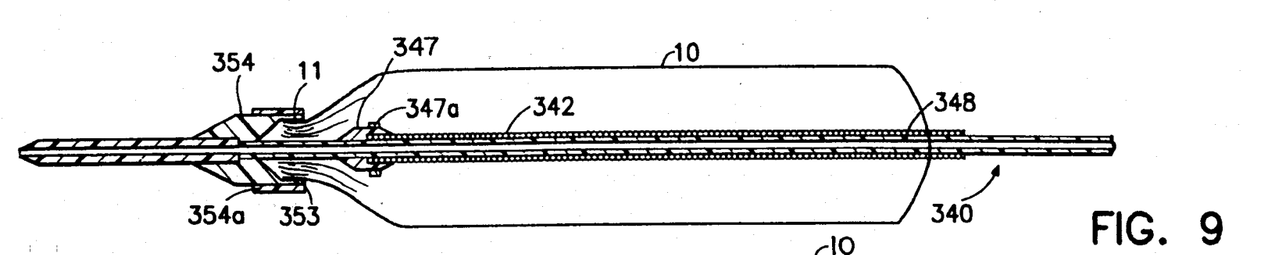
FIGS. 9 and 9a are views similar to FIG. 8a showing the attachment of the distal end of a stent to the introducer.
Figures 9A, 10:
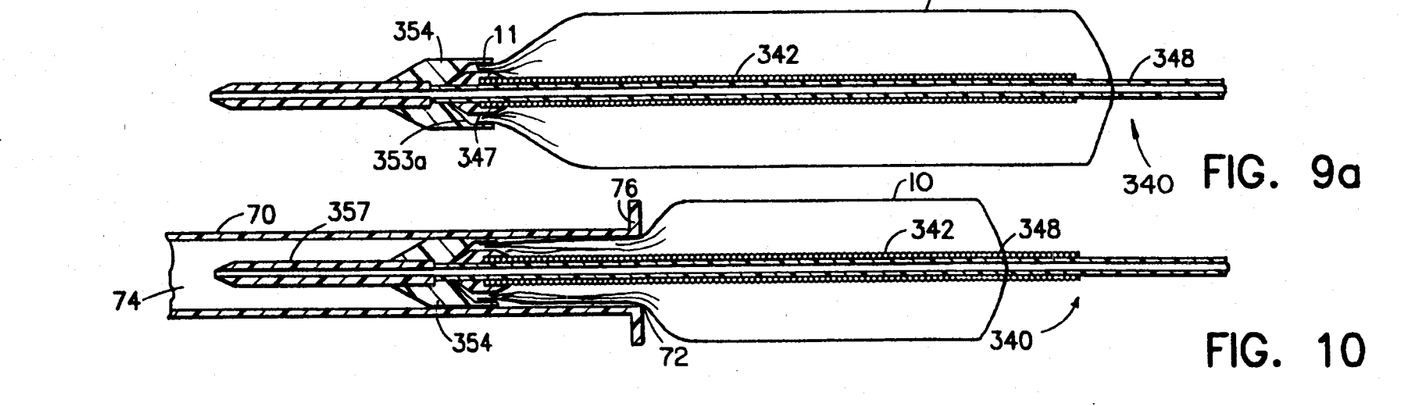
FIGS. 10 and 10a are views similar to FIG. 9 showing the insertion of the introducer into the sheath.
Figure 10A:
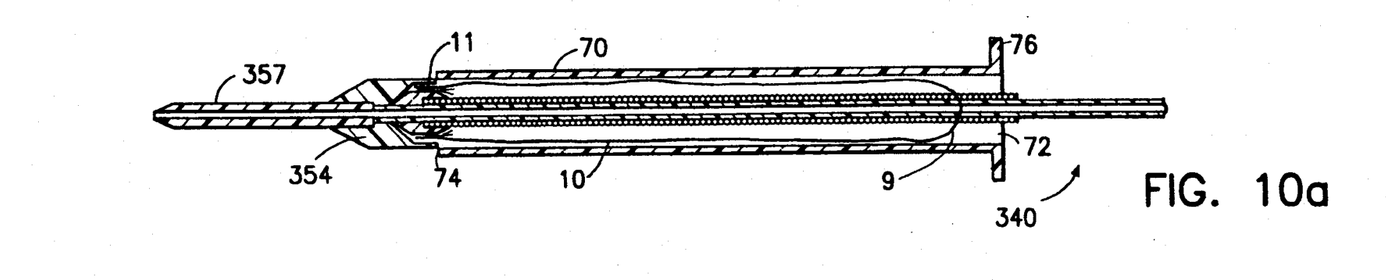

The method of the invention is best understood with reference to FIGS. 9, 9a, 10, 10a, 11, 11a, and 11b. As seen in FIGS. 9, 9a, 10, and 10a, the stent introducer 340 according to the invention is operated by the moving the cap 354 away from the frustroconical tapered locking member 347 as described above with reference to FIGS. 5–7. The distal end 11 of a stent 10 is diametrically compressed and inserted into the cylindrical portion 353 of the cap 354 as shown in FIG. 9. The diametric compression of the distal end of the stent can be facilitated by looping a suture around the distal end of the stent or by using a funnel to insert the distal end of the stent into the cap 354. The cap 354 is then brought into engagement with the frustroconical tapered locking member 347 as described above, thus capturing the distal end 11 of the stent 10. The introducer can be "locked" in this position by use of the locking device 57, 63, 163, 261, 263 or 374 shown and described above with reference to FIGS. 5–8. The distally extending soft catheter tip 357 of the cap 354 is then inserted into the proximal end 72 of a sheath 70 as Shown in FIG. 10. Those skilled in the art will appreciate that as the introducer 340 is inserted into the sheath 70, the outer diameter of the stent 10 is compressed and the length of the stent 10 is extended. While gripping the sheath 70 with the gripping flange 76, the introducer 340 is advanced proximally until the entire stent 10 is enclosed within the sheath 70 and the distally extending soft catheter tip 357 of the cap 354 extends somewhat from the distal end 74 of the sheath 70 as shown in FIG. 10a. When the stent 10, sheath 70, and introducer 340 are assembled in the configuration shown in FIG. 10a, the entire assembly is ready for delivery to the stent deployment site. Guiding the assembly to the stent deployment site may be facilitated through the use of a guide wire as described above. Those skilled in the art will appreciate that a clamping device, such as clamping device 176 in FIG. 8, can be provided on the sheath to clamp it to the introducer and prevent inadvertent movement of the sheath relative to the introducer while the assembly is guided to the deployment site. Generally, however, there is a snug fit between the introducer, stent, and sheath, and therefore, clamping is not necessary.

Figure 11:
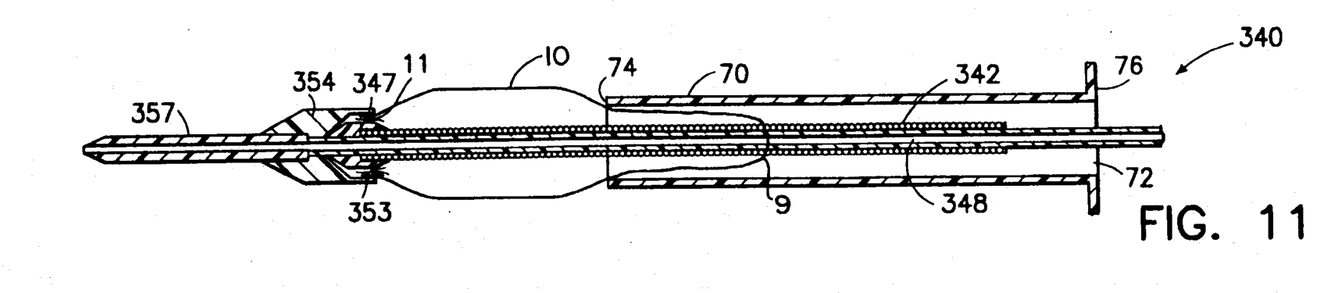
FIGS. 11, 11a, and 11b are views similar to FIG. 10 showing the deployment of the stent by withdrawal of the sheath and releasing it from the distal end of the introducer.
Figure 11A:
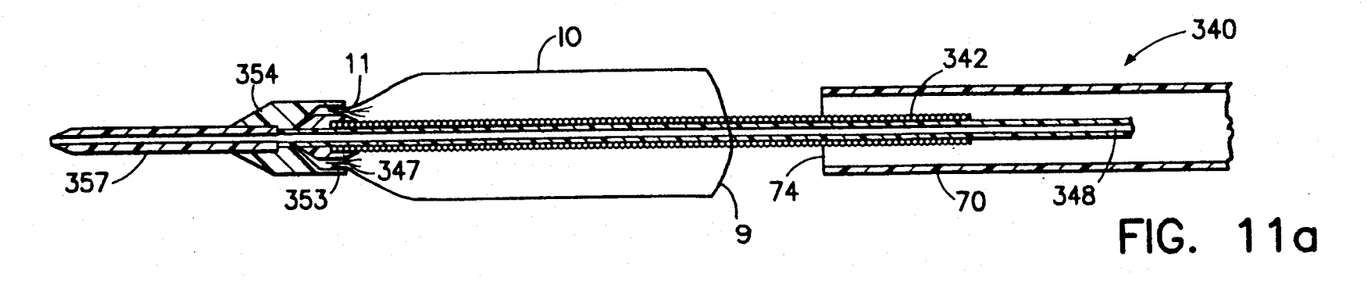
Figure 11B:
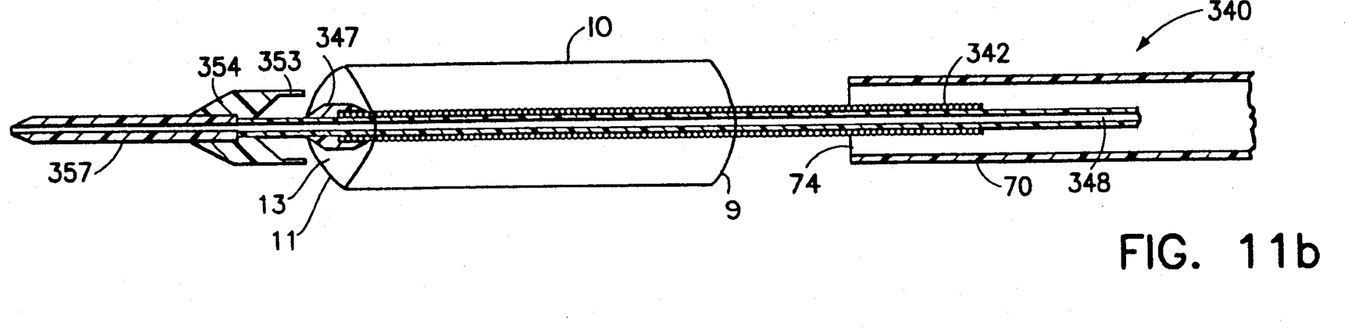

The stent 10 is deployed at the deployment site (not shown) in a sequence of operations described with reference to FIGS. 11, 11a, and 11b. When the introducer 340, stent 10, and sheath 70 are positioned at the deployment site, according to a preferred embodiment, the introducer 340 is held stationary while the sheath 70 is partially withdrawn in a proximal direction as shown in FIG. 11, thereby allowing partial diametric expansion of the stent 10. In this position, the distal end 11 of the stent 10 remains captured between the cap 354 and the tapered locking member 347 and the proximal end 9 of the stent 10 remains covered by the sheath 70. The stent is therefore movable proximally and distally by moving the sheath 70 and the introducer 340 together since the wire ends of the stent are prevented from lodging into the organ wall at the deployment site. When the stent 10 is precisely located, its proximal end 9 is released by further withdrawal of the sheath 70 as shown in FIG. 11a. The release of the proximal end 9 of the stent 10 prevents the stent from being moved proximally. However, so long as the distal end 11 of the stent 10 remains captured by the cap 354 and the tapered locking member 347, the stent can be relocated in the distal direction. The stent 10 is fully deployed when the distal end 11 of the stent is released from the cap 354 and the tapered locking member 347 as described above. In this position, which is shown in FIG. 11b, the stent 10 is diametrically self-expended to engage the organ wall at the deployment site (not shown) and provides a relatively wide lumen 11 through which the introducer 340 may be withdrawn. It will be appreciated that the relative dimensions of the introducer 340, the sheath 70 and the stent 10 should be such that the above described operations are facilitated. Those skilled in the art will appreciate that these dimensions may be varied according to the specific application, i.e., the vessel or organ in which the stent is to be deployed.

In order to facilitate location of the introducer at the site for deployment of the stent, either the end cap 354 or the tapered locking member 347 may be made of radiopaque material or provided with a radiopaque marker such as the circular bands 354a or 347a shown in FIG. 9 so that the apparatus can be located under fluoroscopy. Location of the apparatus may also be assisted by making the introducer "steerable". This can be effected by attaching the distal ends of four wires to the end cap 354 ninety degrees apart from each other. Pulling on the proximal end of one of the wires will bend the end cap in one of four directions thereby "steering" the entire apparatus towards the deployment site. The proximal ends of the four wires could be coupled to a joystick controller at the proximal end of the introducer. Additionally, the exterior surface of the end cap 354 as well as the exterior and interior surfaces of the sheath 70 may be made slippery in any known manner to facilitate operation of the apparatus as described above. Those skilled in the art will appreciate from the above description that the length of the sheath 70 may be equal to the length of the introducer (40, 140, 240, 340) less the length of the stent 11. Alternatively, the length of the sheath may be much shorter than the length of the introducer, so long as it is long enough to contain substantially all of the stent. When the sheath is much shorter than the introducer, the proximal end of the sheath must be provided with an extender coupling mechanism rather than the gripping flange 21. For example, the proximal end of the sheath could be provided with control wire couplings which receive one or more control wires which would extend substantially to the proximal end of the introducer. Withdrawal of the Sheath would be effected by pulling the control wires. It will also be appreciated that a hemostasis valve means can be provided to, prevent blood leakage between the introducer and the sheath and between the introducer and the guide wire.

There have been described and illustrated herein several embodiments of a stent introducer and methods for its use. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other materials could be utilized. It will be recognized that the apparatus of the invention may be made disposable or reusable. Also, while the invention has been disclosed with reference to the delivery and deployment of a stent, it will be understood that the invention is equally useful for the delivery and deployment of a stent-graft or endoluminal graft. Moreover, while particular configurations have been disclosed in reference to handles and locking devices, it will be appreciated that other configurations could be used as well. Furthermore, while the preferred end cap and taper lock have been disclosed as having, mating frustroconical surfaces, it will be understood that different configurations can achieve the same or similar function as disclosed herein. In addition, it will be understood that the length of the sheath may vary according to which embodiment of the invention is implemented. It will therefore be appreciated by those skilled in the art that yet other modifications could be made to the provided invention without deviating from its spirit and scope as so claimed.

I claim:

1. A method for introducing a stent or a stent-graft which is diametrically self-expanding and which is diametrically compressed by axial extension, said method comprising:
    a) providing first and second gripping members, each having a distal gripping end, said first and second gripping members being axially displaceable one relative to the other;
    b) gripping the distal end of the stent or stent-graft between the gripping distal ends of said first and second gripping members;
    c) providing a sheath member having a proximal and a distal end;
    d) inserting the gripped distal end of the stent or stent-graft into the proximal end of the sheath member and advancing the distal end of the stent or stent-graft until it is substantially completely covered by the sheath member;
    e) locating the sheath member, the covered stent or stent-graft, and the first and second gripping members at a site for deploying the stent or stent-graft;
    f) moving one of the sheath member and the first and second gripping members to effect a displacement of the sheath member in a proximal direction relative to the first and second gripping members until the stent or stent-graft is uncovered;
    g) releasing the stent or stent-graft from the first and second gripping members by axially displacing one of said first and second gripping members relative to the other of said first and second gripping members; and
    h) withdrawing the first and second gripping members from the site for deploying the stent or stent-graft.

2. A method according to claim 1, further comprising:
    after said locating and prior to said moving one of the sheath member and the first and second gripping members,
    i) partially withdrawing the sheath member to uncover only a portion of the stent or stent-graft; and
    j) relocating the sheath member, the partially covered stent or stent-graft, and the first and second gripping members at the site for deploying the stent or stent-graft.

3. A method according to claim 2, further comprising:
    after said moving one of the sheath member and the first and second gripping members, and prior to said releasing,
    k) distally relocating the stent or stent-graft, and the first and second gripping members at the site for deploying the stent or stent-graft.

4. A method according to claim 1, further comprising:
    after said gripping and prior to said inserting,
    i) locking the first and second gripping members in the gripping position to prevent the distal end of the stent or stent-graft from premature release from the first and second gripping members.

5. A method according to claim 1, further comprising:
prior to said locating,
i) providing at least one of the first and second gripping members with an axial throughbore;
j) providing a guide wire extending from the site for deploying the stent or stent-graft; and
k) sliding the first and second gripping members over the guide wire with the guide wire extending through the axial throughbore,
wherein
said locating is accomplished by guiding the first and second gripping members along the guide wire.

6. An apparatus for introducing a stent or a stent-graft which is diametrically self-expanding and which is diametrically compressed by axial extension, said apparatus comprising:
a) a hollow tube having a proximal end and a distal end;
b) a control member having a proximal end and a distal end and extending through said hollow tube;
d) an end cap coupled to said distal end of said control member;
e) a sheath member movable relative to said end cap and having a an inner diameter larger than an outer diameter of said hollow tube and smaller than an outer diameter of the stent or stent-graft when the stent or stent-graft is placed in an expanded position, wherein said sheath member extends over at least a portion of said hollow tube, said control member, and the stent or stent-graft when the stent or stent-graft is placed in a contracted position, and movement of one of said sheath member and said end cap relative to the other permits the stent or stent-graft to expand, wherein movement of one of said proximal end of said hollow tube and said proximal end of said control member relative to the other effects an axial displacement of one of said hollow tube and said control member relative to the other from a first position where said end cap covers said distal end of said hollow tube to a second position where said end cap is axially spaced from and uncovers said distal end of said hollow tube.

7. An apparatus according to claim 6, further comprising:
f) an actuation means coupled to said proximal ends of said hollow tube and said control member for effecting an axial displacement of one of said hollow tube and said control member relative to the other from said first position where said end cap covers said distal end of said hollow tube to said second position where said end cap is axially spaced from and uncovers said distal end of said hollow tube, wherein
the distal end of the stent or stent-graft is capturable between said distal end of said hollow tube and said end cap by appropriate manipulation of said actuation means to cause said end cap and hollow tube to assume said first position, and is releasable from between said distal end of said hollow tube and said end cap by appropriate manipulation of said actuation means to cause said end cap and hollow tube to assume said second position.

8. An apparatus according to claim 7, wherein:
said actuation means includes a lever member pivotally connected to a handle member, said handle member being coupled to said proximal end of said hollow tube, and said lever member being coupled to said proximal end of said control member.

9. An apparatus according to claim 7, wherein:
said actuation means includes a finger grip means coupled to one of said proximal end of said hollow tube and said proximal end of said control member, and a handle coupled to the other of said proximal end of said hollow tube and said proximal end of said control member.

10. An apparatus according to claim 9, wherein:
said finger grip comprises a spool and said handle comprises a slotted shaft,
said control member is coupled to said slotted shaft, and
said hollow tube is coupled to said spool.

11. An apparatus according to claim 10, wherein:
said end cap and said control member are provided with axial throughbores for receiving a guide wire, and
said slotted handle is provided with a proximal throughbore which communicates with the throughbore in said control member.

12. An apparatus according to claim 11, wherein:
said proximal throughbore is at least partially defined by a luer coupling.

13. An apparatus according to claim 7, wherein:
said actuation means comprises a ratchet member coupled to one of said proximal end of said hollow tube and said proximal end of said control member and a handle coupled to the other of said proximal end of said hollow tube and said proximal end of said control member, said handle having a lever member for engaging said ratchet member.

14. An apparatus according to claim 7, wherein:
said actuation means includes locking means for locking said hollow tube and said end cap in said first position.

15. An apparatus according to claim 14, wherein:
said locking means is selected from the group consisting of a hook and eyelet, a set screw, and a latch.

16. An apparatus according to claim 6, wherein:
said hollow tube is a flexible coil having an outer surface covered with a thin flexible covering.

17. An apparatus according to claim 6, wherein:
said control member is a flexible member covered with a braided covering to inhibit axial stretching.

18. An apparatus according to claim 6, wherein:
said end cap and said control member are provided with axial throughbores for receiving a guide wire.

19. An apparatus according to claim 6, wherein:
said end cap has a concave portion which covers said distal end of said hollow tube when said end cap and said distal end of said hollow tube are in said first position.

20. An apparatus according to claim 6, wherein:
said sheath member is provided with a proximal gripping flange.

21. An apparatus according to claim 6, wherein:
said sheath member is provided with a proximal hemostasis valve means.

22. An apparatus for introducing a stent or a stent-graft which is diametrically self-expanding and which is diametrically compressed by axial extension, said apparatus comprising:
a) a hollow tube having a proximal end, and a distal end having a substantially frustroconical cover;
b) a control member having a proximal end and a distal end and extending through said hollow tube;

d) an end cap coupled to said distal end of said control member;
e) an actuation means coupled to said proximal ends end of said hollow tube and said control member for effecting axial displacement of one of said hollow tube and said control member relative to the other from a first position where said end cap covers said distal end of said hollow tube to a second position where said end cap is axially spaced from and uncovers said distal end of said hollow tube, wherein the distal end of the stent or stent-graft is capturable between said distal end of said hollow tube and said end cap by appropriate manipulation of said actuation means to cause said end cap and hollow tube to assume said first position, and is releasable from between said distal end of said hollow tube and said end cap by appropriate manipulation of said actuation means to cause said end cap and hollow tube to assume said second position.

23. An apparatus according to claim 22, wherein:
said end cap has a substantially frustroconical interior surface.

24. An apparatus according to claim 23, wherein:
said end cap and said control member are provided with axial throughbores for receiving a guide wire.

25. An apparatus according to claim 24, wherein:
said end cap is provided with a distally extending soft catheter tip.

* * * * *